US006907298B2

(12) United States Patent
Smits et al.

(10) Patent No.: US 6,907,298 B2
(45) Date of Patent: Jun. 14, 2005

(54) METHOD AND APPARATUS FOR IMPARTING CURVES IN IMPLANTABLE ELONGATED MEDICAL INSTRUMENTS

(75) Inventors: Karel F. A. A. Smits, Munstergeleen (NL); Jean J. G. Rutten, Bocholtz (NL); Paulus G. Adams, Munstergeleen (NL)

(73) Assignee: Medtronic, Inc., Minneapolis, MN (US)

( * ) Notice: Subject to any disclaimer, the term of this patent is extended or adjusted under 35 U.S.C. 154(b) by 254 days.

(21) Appl. No.: 10/045,850

(22) Filed: Jan. 9, 2002

(65) Prior Publication Data

US 2003/0130712 A1 Jul. 10, 2003

(51) Int. Cl.[7] ............................................... A61N 1/05
(52) U.S. Cl. .................. 607/125; 607/122; 604/524; 604/526
(58) Field of Search ............................ 607/117–130; 604/523–532, 95.01–95.05, 264; 600/121, 139–150, 380, 381, 433–435; 606/191, 194

(56) References Cited

U.S. PATENT DOCUMENTS

| | | | |
|---|---|---|---|
| 3,521,620 A | 7/1970 | Cook ......................... | 128/2.05 |
| 3,547,103 A | 12/1970 | Cook et al. ................ | 128/2.05 |
| 3,610,231 A | * 10/1971 | Takahashi et al. .......... | 600/139 |
| 4,136,703 A | 1/1979 | Wittkampf .............. | 128/419 P |
| 4,381,013 A | 4/1983 | Dutcher ..................... | 128/785 |
| 4,458,677 A | 7/1984 | McCorkle, Jr. ............. | 128/786 |
| 4,479,500 A | 10/1984 | Smits ......................... | 128/786 |
| 4,676,249 A | 6/1987 | Arenas et al. .............. | 128/657 |
| 4,677,990 A | 7/1987 | Neubauer ................... | 128/786 |
| 4,815,478 A | 3/1989 | Buchbinder et al. ........ | 128/772 |
| 4,898,577 A | 2/1990 | Badger et al. ................ | 604/53 |
| 4,917,104 A | * 4/1990 | Rebell ........................ | 600/585 |
| 4,940,062 A | 7/1990 | Hampton et al. ........... | 128/772 |
| 5,040,543 A | 8/1991 | Badera et al. .............. | 128/772 |
| 5,125,395 A | 6/1992 | Adair ............................. | 128/4 |
| 5,170,787 A | 12/1992 | Lindegren ................... | 128/642 |
| 5,327,906 A | 7/1994 | Fideler ....................... | 128/772 |
| 5,368,564 A | 11/1994 | Savage ........................ | 604/95 |
| 5,378,234 A | 1/1995 | Hammerslag et al. | |
| 5,396,902 A | 3/1995 | Brennen et al. ............ | 128/772 |
| 5,433,200 A | 7/1995 | Fleischhacker ............. | 128/657 |
| 5,439,006 A | 8/1995 | Brennen et al. ............ | 428/772 |
| 5,477,856 A | 12/1995 | Lundquist ................... | 128/642 |
| 5,545,200 A | 8/1996 | West et al. .................. | 607/122 |
| 5,562,619 A | 10/1996 | Mirarchi et al. .............. | 604/95 |
| 5,662,119 A | 9/1997 | Brennen et al. ............ | 128/772 |

(Continued)

FOREIGN PATENT DOCUMENTS

| | | |
|---|---|---|
| EP | 1 010 440 A2 | 12/1999 |
| JP | 63281618 | 11/1988 |

*Primary Examiner*—Jeffrey R. Jastrzab
(74) *Attorney, Agent, or Firm*—Girma Wolde-Michael; Paul H. McDowall; Michael C. Soldner

(57) ABSTRACT

Elongated medical instruments adapted to be permanently or temporarily implanted in the mammalian body or used to access a site in the body to facilitate introduction of a further medical device, and methods and apparatus for deflecting the distal end and imparting curves in distal segments of such medical instruments within the body by manipulation of a proximal segment of the instrument outside the body are disclosed. Multiple portions of distal segments of a single one or distal segments of coaxially arranged distal segments of deflectable coiled wires are formed each having a line of spacers each functioning as a backbone along a side of the wire coil and formed in a variety of ways. One or more elongated movable wire extends through a coil lumen to one or more attachment point distal to each portion that can be pushed to widen and/or pulled to narrow the spacing of coil turns across the coil diameter from the line to induce a bend in all more proximal portions.

20 Claims, 6 Drawing Sheets

U.S. PATENT DOCUMENTS

| | | | |
|---|---|---|---|
| 5,722,425 A | 3/1998 | Bostrom | 128/772 |
| 5,728,148 A | 3/1998 | Bostrom et al. | 607/116 |
| 5,755,760 A * | 5/1998 | Maguire et al. | 607/122 |
| 5,797,905 A * | 8/1998 | Fleischman et al. | 606/41 |
| 5,824,031 A | 10/1998 | Cookston et al. | 607/122 |
| 5,879,295 A * | 3/1999 | Li et al. | 600/373 |
| 5,882,333 A | 3/1999 | Schaer et al. | 604/95 |
| 5,931,830 A | 8/1999 | Jacobsen et al. | 604/523 |
| 5,999,858 A * | 12/1999 | Sommer et al. | 607/122 |
| 6,059,739 A | 5/2000 | Baumann | 600/585 |
| 6,146,138 A | 11/2000 | Dalmau | 433/141 |
| 6,321,123 B1 * | 11/2001 | Morris et al. | 607/122 |
| 6,471,699 B1 * | 10/2002 | Fleischman et al. | 606/41 |
| 6,500,172 B1 * | 12/2002 | Panescu et al. | 606/31 |

* cited by examiner

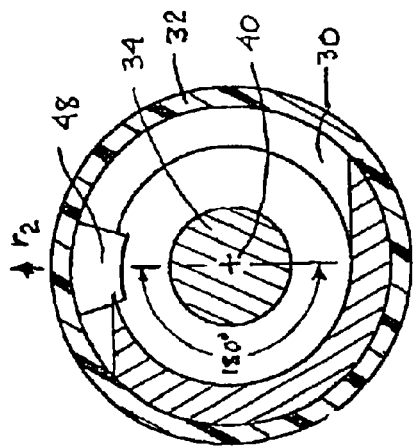
FIG. 4
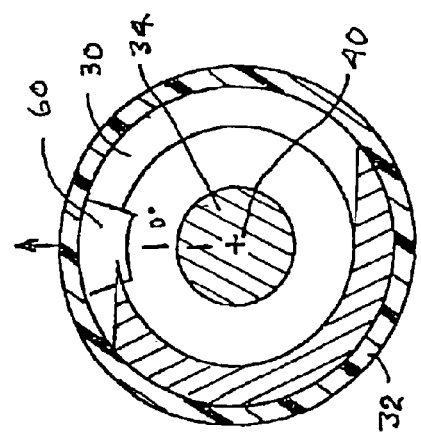
FIG. 5
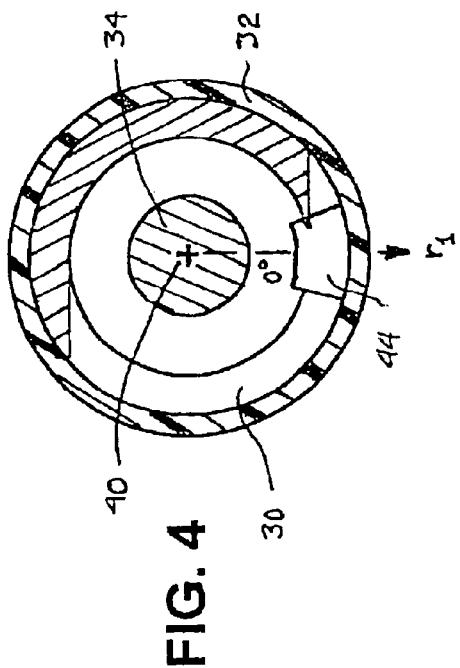
FIG. 7
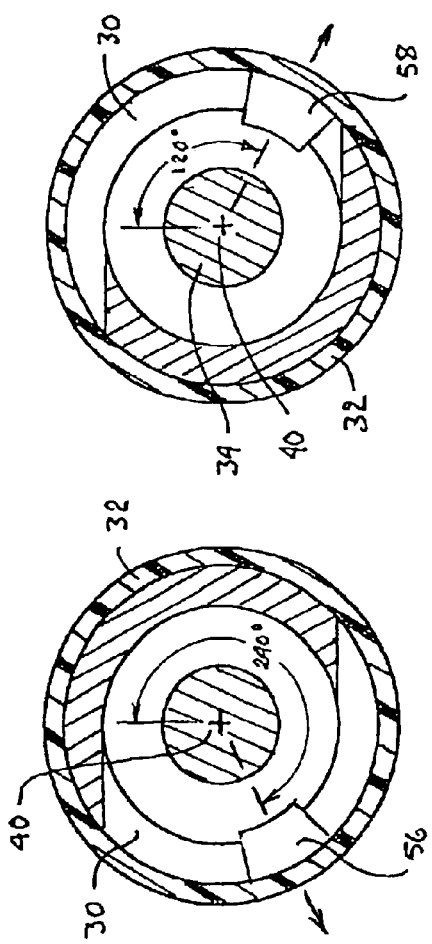
FIG. 8
FIG. 9

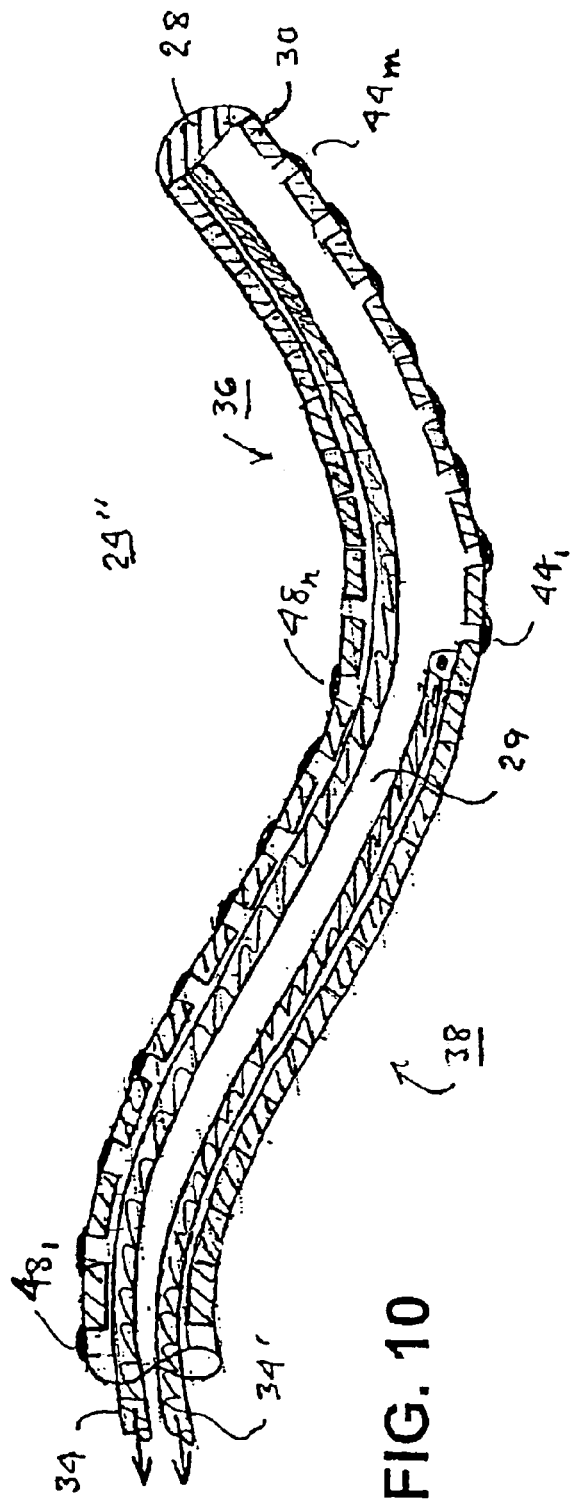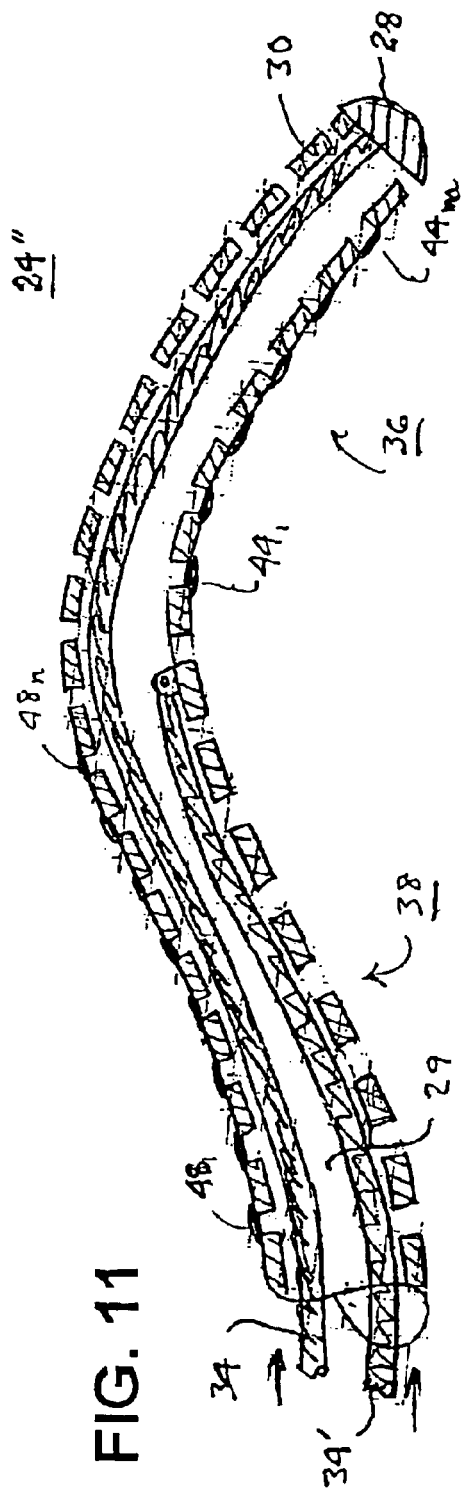

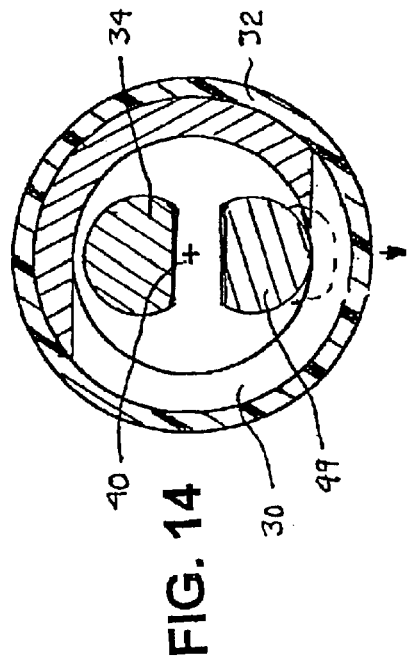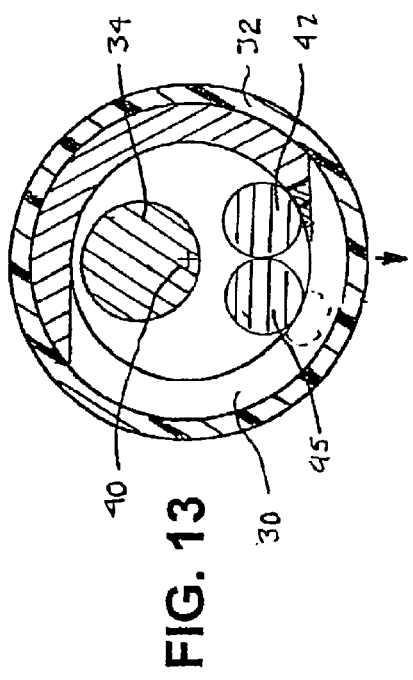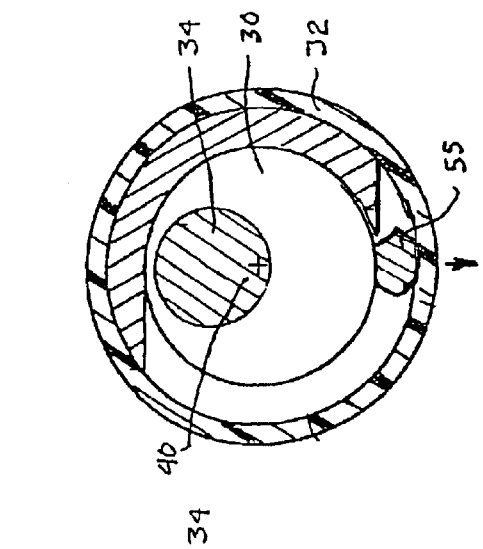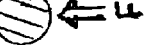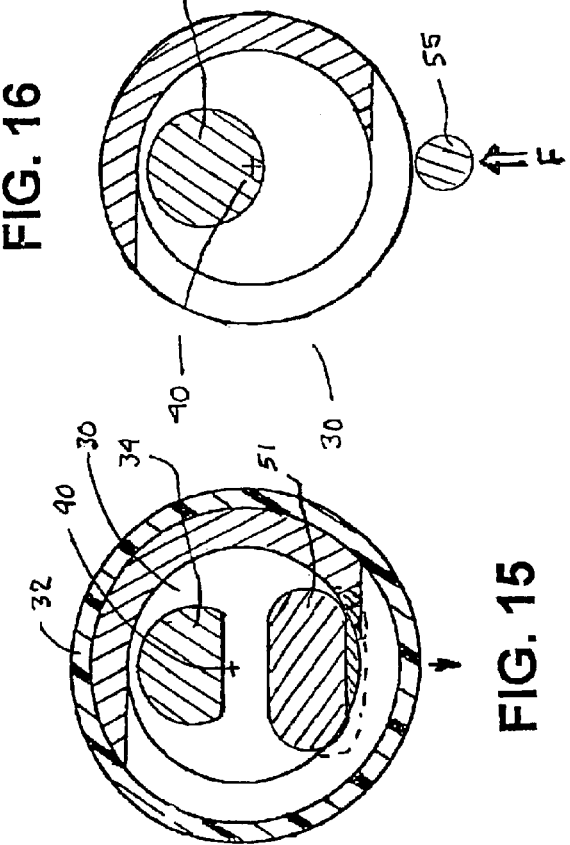

METHOD AND APPARATUS FOR IMPARTING CURVES IN IMPLANTABLE ELONGATED MEDICAL INSTRUMENTS

FIELD OF THE INVENTION

The present invention pertains to elongated medical instruments adapted to be permanently or temporarily implanted in the mammalian body or used to access a site in the body to facilitate introduction of a further medical device, and particularly to methods and apparatus for deflecting the distal end and imparting curves in distal segments of such medical instruments within the body by manipulation of a proximal segment of the instrument outside the body.

BACKGROUND OF THE INVENTION

A wide variety of elongated medical instruments that are adapted to be permanently or temporarily implanted in the mammalian body, usually the body of a human patient, or used to access a site in the body to facilitate introduction of a further medical device. Such elongated medical instruments have an instrument body extending between instrument body proximal and distal ends, and a distal segment of the instrument body is advanced to a remote site in the body by manipulation of a proximal segment of the instrument body or a handle or stylet or the like extending from the instrument body proximal end located outside the body.

Elongated medical instruments include implantable medical electrical leads, catheters, guidewires, stylets and the like. In the case of a medical electrical lead, the lead body proximal end is coupled to an implantable pulse generator (IPG) or monitor that is then implanted subcutaneously or to an external medical device located outside the body and electrical signals are conducted to or from the remote site in the body through one or more lead conductor. Catheters typically extend through the patient's skin and are coupled with external diagnostic or therapeutic equipment or are used to introduce other elongated medical instruments or fluids or the like, or to withdraw fluids or measure pressure, or the like, through a catheter lumen open at the accessed remote site. Certain catheters, e.g., electrophysiology ablation and mapping catheters, also deliver electrical energy or conduct electrical signals of the body. Other catheters include pulmonary artery catheters, central venous catheters, diagnostic coronary catheters, intra-aortic balloon pump catheters, balloon tipped (PTCA)/angioplasty catheters, and cardiac stent delivery catheters. The terms "catheter" and "lead" are often interchanged in these and other contexts.

Guidewires are small diameter wires that are directed through tortuous pathways to provide for advancement of open-ended medical leads or catheters having guidewire receiving lumens over-the-wire. Certain guidewires are also designed to function as a micro-catheter for infusion of fluids through a guidewire lumen. Other guidewires include insulated electrical conductors connected at the guidewire proximal end with an external medical device to deliver electrical energy for tissue stimulation or to conduct electrical signals of the body to the external medical device.

Stylets are small diameter wires that are inserted into lumens of closed end electrical medical leads to stiffen the assemble and provide directional control enabling the assembly to be advanced through pathways, e.g., transvenous pathways, in the body to lodge electrodes and/or sensors on the lead body at a desired site.

Hence, in the following discussion, the term elongated medical instrument relates to and embraces such electrical medical leads, catheters, stylets, and guidewires having directional control enabling deflection of a distal tip or inducement of a curve or bend in one or more distal portion of the instrument body from a proximal portion accessible outside the body.

In many cases, the introduction of such elongated medical instruments to a remote site in the body is effected through a skin incision accessing an incision into a blood vessel, whereby the instrument body is advanced through a vascular pathway until the distal segment or the instrument body distal end are located at the remote site. Such advancement is often through a tortuous pathway having twists and turns requiring the capability to impart a curve or deflect the instrument body distal end to facilitate advancement. Therefore, the introduction of such elongated medical instruments through vascular pathways or other tortuous pathways in the body is facilitated by a wide variety of techniques and mechanisms that have been developed to impart curves in the distal segment of the instrument body or to deflect the instrument body distal end.

Currently, during the implantation of a permanent cardiac pacemaker or an implantable cardioverter/defibrillator (ICD), endocardial cardiac leads, e.g., pacing leads and/or cardioversion/defibrillation leads, are introduced into a vein either via a cut down or percutaneous sheath introduction. The cardiac leads are advanced under fluoroscopy into either the right atrium, right ventricle (or both in the case of a dual chamber pacemaker or ICD implantation) or into a cardiac vessel, e.g., the coronary sinus and great vein. Generally speaking, it is highly desirable that such cardiac leads be so flexible through their length that they are capable of flexing with the movement of the heart and other muscular movement so as to void the fracture of the lead body due to its cumulative stressing. Such cardiac lead bodies are generally too limp to be advanced axially on their own through the vascular pathway to the desired site in a heart chamber or vessel. It has been commonplace for many years to employ thin wire stiffening stylets extended down a lumen of the lead body to stiffen the entire assembly so that it can be pushed axially through the venous pathway: Then, the distal pace/sense electrodes or cardioversion/defibrillation electrodes (herein "cardiac electrodes") must be fixed at the preferred site in the heart chamber or vessel to operate most efficaciously and to prevent dislodgement. The introduction and fixation of these cardiac leads is the most time consuming and difficult aspect of the implantation.

At the outset, a straight or slightly curved stiffening stylet is first extended into the lead body lumen within the cardiac lead in order to give the cardiac lead sufficient column strength and rigidity to be pushed through the tributary veins and typically into the subclavian vein. The stylet may be left straight or provided with a certain degree of curvature to facilitate the introduction through these veins and through the initial curvatures thereof. Thereafter, and from time to time, as the physician directs the distal tip of the cardiac lead in a tortuous path leading to the right heart through the superior vena cava (SVC), it may be necessary to withdraw the stylet and either substitute a new stylet or impart a different curvature to the distal segment of the stylet, reinsert the stylet, and advance the distal segment of the lead a bit further until another obstacle to advancement is encountered.

When the distal cardiac electrodes are to be placed in the right ventricle, the physician manually fashions a curve at the tip of another stylet that is inserted into the lead body lumen to advance the assembly through the tricuspid valve into the right ventricle. Most physicians continue advancing the lead with the curved tip stylet in place into the pulmonary artery outflow track to confirm right ventricle access and to rule out the possibility of entrance into the coronary sinus or coronary vein, which can mimic the appearance of a right ventricle placement under fluoroscopy. The conventional practice requires the physician to then remove the curved stylet and partially re-advance the original or another straight stylet into the lead body lumen, once the physician has confirmed that the lead is in fact in the pulmonary outflow track. The cardiac lead is then carefully pulled back under direct fluoroscopic observation until the lead body distal segment drops from the proximal portion of the pulmonary artery to the floor of the right ventricle. The physician then advances the stylet to its fully advanced position within the lead body lumen and advances the lead distal end into the right ventricular apex. Passive or active fixation mechanisms at the lead body distal end then effect fixation with the trabeculae or the myocardium to acutely maintain the cardiac electrode(s) at the operative site.

In the case of atrial lead placement, the lead body distal end is typically lodged or affixed in the right atrial appendage which results in the lead body extending into the right atrium via the SVC and then bent through about a 180° or greater bend.

Over the years, many atrial cardiac lead designs and atrial cardiac lead introduction tools and techniques have been proposed or clinically used to both achieve this orientation and to fix the cardiac lead body distal end within the atrial appendage and avoid dislodgement. Initially, such atrial cardiac leads were formed with a permanent "J"-shaped bend to facilitate both the positioning and the retention of the atrial electrode in the patient's atrial appendage as taught, for example, in U.S. Pat. No. 4,136,703. Insertion of these "J"-shaped leads is greatly facilitated through the use of a straight solid inner stylet which, in this case, straightens the bend normally fixed within the distal end of the lead itself to the extent that the stylet is advanced into or retracted from the lead body lumen.

Moreover, it has been proposed to combine atrial and ventricular leads together or in a cooperative relation to provide a "single pass" implantation of both leads as set forth in U.S. Pat. Nos. 4,458,677 and 4,479,500 and patents referenced therein. Such proposed single pass AV leads have not gained acceptance due to their complicated construction, use and size.

J-shaped atrial leads have largely been abandoned in favor of reduced diameter lead bodies that cannot accommodate shape-forming structures and the use of the straightening stylet as described above. Today, the small diameter cardiac lead body is normally straight, and the lead body distal end is typically aimed into the atrial appendage employing multiple insertions of relatively straight and curved stylets. The electrode bearing lead body distal end is fixed in the atrial appendage by means of an active fixation screw or passive fixation tines. However, dislodgements can occur before the fixation is effected when a stylet is withdrawn proximally as the stylet may bind against the lead body lumen in the region of the bend.

Thus, there are multiple exchanges of straight stylets and curved stylets, which have been bent according to the physician's choice in a typical cardiac lead implantation in the right atrium and ventricle. Similar techniques and multiple stylets are avoided to advance a cardiac lead distal segment into the coronary sinus and great vein. Stylets are typically formed of solid wire, typically about 0.014–0.018 inches in diameter. During handing, such stylets can easily become bent or kinked, and thereafter cause great difficulty when an attempt is made to reinsert them through the narrow inner diameter of the lead body lumen, which may only be 0.019 inch in the case of a stylet of 0.018 inch diameter, thereby providing no more than 0.0005 inch clearance around the circumference. The continual withdrawal and reintroduction of stylets is time consuming and offers the potential of damaging the lead in the process.

Moreover, it is undesirable to contaminate the lead body lumen with blood during this process because drying blood can form a strong adhesive bond between the stylet and the lumen wall, making stylet removal impossible and rendering the lead unusable. Because the surgeon is working through an open wound, even the most fastidious surgeon will have blood on his gloves that can be transferred to the stylet. The blood congeals, and because of the small clearance, even a few drops of blood are sufficient to causing jamming of the stylet inside the lead body lumen. When the stylet jams in the lead body lumen, kinking of the stylet within the lead can occur, which kinks, in turn, will create new jams or problems with the insertion and retraction of the stylet from the lead body lumen. In some cases, the jamming is so severe that the cardiac lead must be removed from the heart for fear of insulation puncture, discarded, and a new lead implanted, thereby at least doubling the lead cost used in the procedure as well as operative time. The overall result of such difficulties is that operative time is greatly increased which results in increased time delay, associated cost, and prolonged X-ray exposure to the patient under continuous fluoroscopy as well as prolonged scattered X-ray exposure to the operating room staff due to procedural time delays. These problems with the use of multiple stiffening stylets have been recognized in the art as set forth in U.S. Pat. Nos. 4,136,703, 4,381,013, 4,677,990, 5,662,169, 5,824,031, and 6,059,739, for example.

Many proposals have been advanced to reduce the number of stylets and the consequent number of times that stylet removal and re-insertion that are needed in the procedure. One approach has been to employ deflectable stylets wherein the stylet distal segment can be deflected or curved while within the lead body lumen from the proximal end thereof. Two-piece stylets that comprise a straight, tubular outer member and a curved inner member received within the outer member lumen enabling relative movement of the inner and outer members are disclosed in the above-referenced '703 and '013 patents for straightening a J-shaped bend and in U.S. Pat. Nos. 5,722,425 and 5,728, 148. The outer tubular member of the '013 patent enables the transmission of torque applied by the implanting physician at the proximal end to be transmitted to a fixation helix located at the lead body distal end lead to screwed the helix into endocardial tissue. Alternatively, two-piece stylets comprising a curved outer member and a relatively straight inner member are also known to the art, as disclosed in U.S. Pat. Nos. 4,676,249 and 5,040,543. In such composite stylets, the relative position of the inner member with respect to the outer member determines the degree to which the curved member (inner or outer) is allowed to display its preset curvature.

A commonly employed approach to providing controllable deflection of the distal end segments of catheters and guidewires employs a generally straight outer sheath and a pull or push or push-pull wire extending through a lumen of the outer sheath to an attachment point at the sheath distal end. The wire is pushed or pulled on at its proximal end typically through a handle that is permanently or removably attached to the catheter or guidewire proximal end. The proximal retraction or distal advancement of the pull or push wire, respectively, causes at least a distal segment of the outer sheath to bend or deflect. Examples of such deflection mechanisms in catheters can be found in U.S. Pat. Nos. 3,547,103, 3,521,620, 4,815,478,4,898,577, 4,940,062, 5,125,395, and 5,545,200. U.S. Pat. Nos. 4,815,478 and 4,940,062 disclose the use of push-pull wires extending through guidewire lumens for deflecting the guidewire distal end by manipulating a handle at the guidewire proximal end. Deflectable stylets intended to be inserted into cardiac lead body lumens employing this type of deflection mechanism are disclosed in U.S. Pat. Nos. 5,662,119, 5,170,787, and 5,327,906, 5,396,902, 5,439,006, 6,059,739, and 6,146,138.

Spring wire guidewires and/or stylets are disclosed in the above-referenced '395, '620, and '338 patents that have pull wires extending from a proximal handle at the proximal end of the stylet or guidewire shaft through the lumen of the coiled wire body or shaft and to an attachment at the distal end of the coiled wire shaft. It is desirable to be able to control the direction of deflection of the distal segment so that it always bends in a known direction when the pull wire or push-pull wire is retracted or extended from the proximal handle. Linear attachment mechanisms are also provided in the distal segments of the coiled wire shaft that attach the adjacent coils together in a line parallel to the segment of the pull wire extending through the lumen so that the coil turns cannot be stretched apart or compressed together along that side of the segment. In the '620 patent, a short wire is disposed in and partially obstructs the lumen, and the coiled wire turns are welded to it. Several linear attachment mechanisms, characterized as "backbone" members, are disclosed in the '338 patent that are shaped to extend between the coil turns and to minimize the obstruction of the lumen. In the '395 patent, the coil turns are soldered together in the line. A further U.S. Pat. No. 5,931,830 discloses spot welding adjacent coils together to increase torqueability of a coiled wire guidewire rather than to control its direction of bending.

In a further variation, U.S. Pat. No. 5,477,856 discloses several embodiments of torqueable tubular members that are formed of a tube having one or more pull wire extending through the tube lumen to one or more distal attachment point. Segments are cut away from the stainless steel or shape memory alloy tube leaving a backbone bridging the cut away segment that is bendable upon retraction of the pull wire(s). In at least one embodiment, a plurality of adjoining cutaway tube segments are formed that are radially displaced by 30°–120°, for example, from one another to form a flex segment. A further plurality of flex segments, having the same number or differing numbers of cutaway tube segments are formed along sections of the tube. The cutaway tube segments can have the same or differing widths and separations apart from one another.

While all of the mechanisms disclosed in the above cited prior art patents are at least to some degree workable, there is still a perceived need for a mechanism that is simple, inexpensive to manufacture, does not excessively increase the elongated medical instrument body diameter, and can be manipulated using one hand to control the deflection and imparted curvature of the instrument body distal segment More significantly, there is a need for a such a mechanism that eliminates the need for separate curved stylets used to deflect and impart curves in the medical instrument distal segment and which provides a wide degree of dynamic curvature to the elongated medical instrument being advanced by the physician.

SUMMARY OF THE INVENTION

The present invention accomplishes these needs through mechanisms for controlling the deflection of discrete portions of distal segments of deflectable wires, particularly space wound wire coils that are joined together by lines of spacers that are uniquely configured to simplify fabrication.

In one variation of the invention, multiple portions of distal segments of a single one or distal segments of coaxially arranged distal segments of deflectable coiled wires are formed each having a line of spacers each functioning as a backbone along a side of the wire coil. A single elongated movable wire extends through a coil lumen to an attachment point distal to each portion, which can be the distal tip of the wire coil. Or separate movable wires extend through the coil lumen, or lumens in coaxially arranged deflectable wires, and are attached at their distal ends to attachment point distal to each portion. The movable wire(s) can be pushed to widen and/or pulled to narrow the spacing of coil turns across the coil diameter from the line to induce a bend in all more proximal portions. In one variation, the backbone located within a portion of the coil lumen, extending along one side of the coil and mechanically coupled to the a plurality of turns of the wire coil to maintain the spacing between coil turns and induce a bend in the portion of the coil when the movable wire is pulled or pushed has a width greater than its arc height and presents a flattened or arcuate surface facing the surface of the movable wire extending alongside the backbone. The movable wire can be formed having a flattened surface along at least a portion of its length extending alongside the pair of short wires within the coil lumen to maximize spacing between them to minimize binding.

The line of spacers can be formed by welding a pair of small diameter short wires disposed side-by-side alongside one another within the coil lumen and welded to coil turns. The line of spacers can alternatively or additionally be formed of a weld feed wire welded alongside the exterior of the wire coil to flow between the wire coil turns.

The proximal segments of each such deflectable wire comprises an elongated tubular member that can be formed of a solid tube of metal or reinforced plastic. Alternatively, the elongated tubular member and wire coil are formed of a single elongated wire coil having proximal and distal segments, and the wire coil turns in the proximal segment are tightly wound and/or welded together at spaced apart longitudinal and radial locations to create torque control while maintaining flexibility.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 4 is a cross-section view taken along lines 4—4 of FIG. 2 depicting the angular orientation of the first line of spacers depicted in FIG. 2;

FIG. 5 is a cross-section view taken along lines 5—5 of FIG. 3 depicting the angular orientation of the first line of spacers depicted in FIG. 2;

FIG. 7 is a cross-section view taken along lines 7—7 of FIG. 6 depicting the angular orientation of the first line of spacers depicted in FIG. 6;

FIG. 8 is a cross-section view taken along lines 8—8 of FIG. 6 depicting the angular orientation of the second line of spacers depicted in FIG. 6;

FIG. 9 is a cross-section view taken along lines 9—9 of FIG. 6 depicting the angular orientation of the third line of spacers depicted in FIG. 6;

FIGS. 10 and 11 are plan views in partial cross-section of the distal segment of a steerable stylet wire in accordance with a variation of the embodiments of the present invention employing separate movable wires for each portion of the distal segment of the stylet wire wherein the movable wires are pushed distally or pulled proximally selectively to induce curvatures in the distal segment of the stylet wire;

FIGS. 13–15 are cross-section views of the portions of the stylet wire distal segments depicting short wires fitted into the coiled wire lumens of the leads and welded in place to form lines of spacers; and FIGS. 16 and 17 are cross-section views depicting the formation of lines of spacers from weld supply wire applied to the exterior of the coiled wire turns and welded in place.

DETAILED DESCRIPTION OF THE PREFERRED EMBODIMENTS

In the following detailed description, references are made to illustrative embodiments for carrying out the invention. It is understood that other embodiments may be utilized without departing from the scope of the invention. To simplify the description, the various illustrative embodiments and variations of the invention are described in the context of a steerable stylet, but it will be understood the invention is applicable to elongated medical instruments including stylets used in the introduction of medical electrical leads, guidewires used in the introduction of various types of catheters, and in specialized microcatheters used for a variety of purposes in the body. It will be understood that the present invention can be utilized in any elongated medical instruments of the types described or mentioned herein and equivalents that may presently exist or come into existence in the future to introduce or guide various medical devices into the body.

Figure 1:
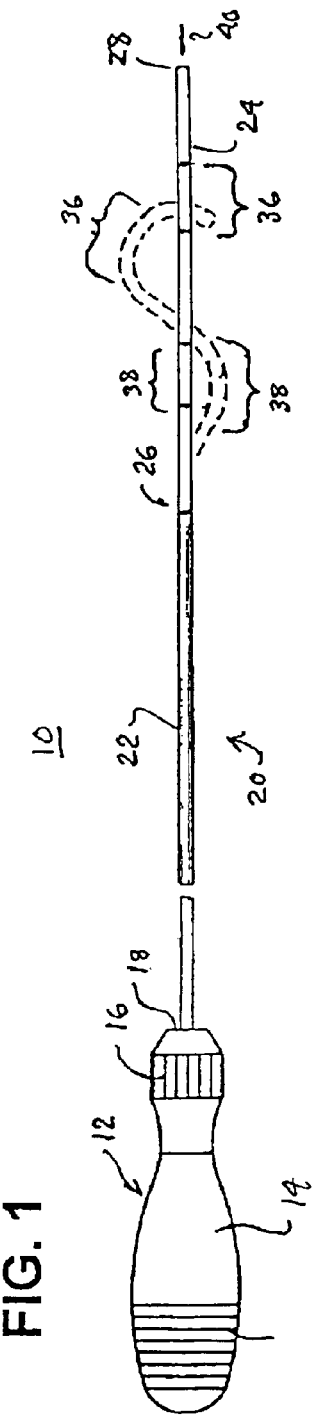
FIG. 1 is a plan view of a steerable stylet in accordance with a first embodiment of the present invention capable of forming a compound, substantially two-dimensional, curve in the distal segment of the stylet wire.

FIG. 1 illustrates a deflectable stylet 10 according to the present invention comprising a handle 12 and an elongated stylet wire 20. The handle 12 includes a main handle portion 14 and a spinner or knob 16, mounted rotatably with respect to the primary handle portion 14. The elongated stylet wire 20 that from a proximal recess 18, within spinner or knob 16 of handle 12. The handle 12 preferably takes the form of that disclosed in the above-referenced, commonly assigned '338 patent.

The elongated stylet wire 20 has a predetermined length extending from a proximal stylet wire end within handle 12 and a distal stylet wire end 28. The stylet wire further comprises a proximal segment 22 and a distal segment 24 that are joined together at junction 26 in end-to-end abutting or overlapping relationship.

The proximal segment 22 preferably comprises an elongated tubular member or tube extending through a predetermined tube length from a proximal tube end fixed within handle 12 and a distal tube end at the junction 26. A tube lumen extends through the tube from within the handle 12 to the distal tube end at junction 26. The elongated tube may be fabricated of a superelastic NITINOL alloy, stainless steel or another appropriate metal and which may take the form, for example, of a length of hypodermic tubing, preferably stainless steel, super-precision drawn, smooth-bore tubing.

Figure 2:
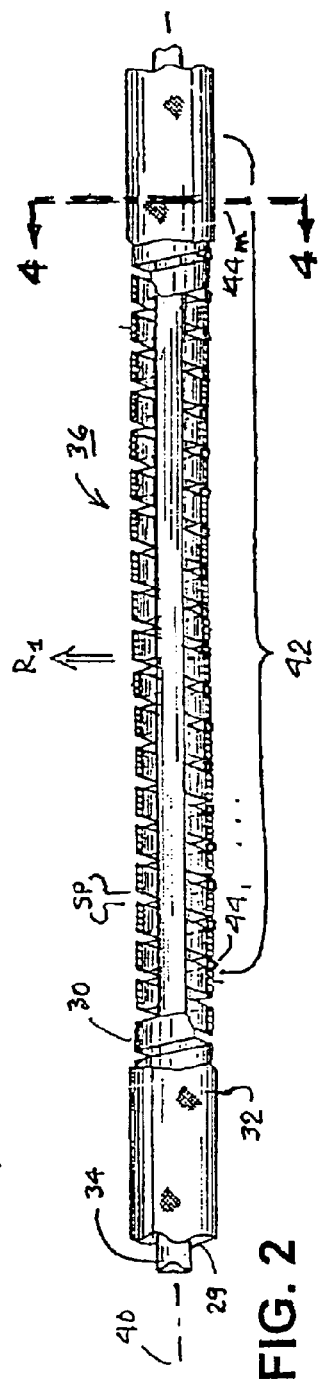
FIG. 2 is a partially exposed, side view of a first portion of the distal segment of the steerable stylet wire of FIG. 1.
Figure 3:
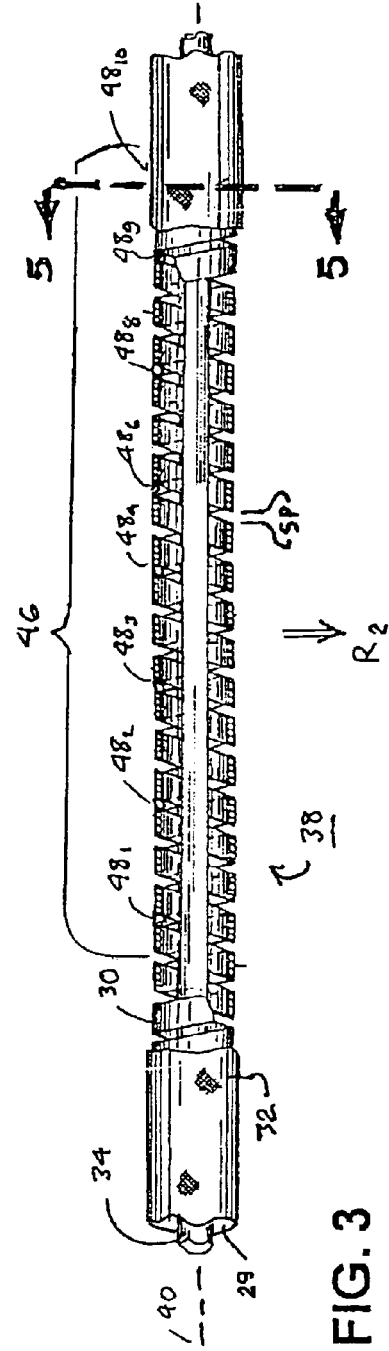
FIG. 3 is a partially exposed, side view of a second portion of the distal segment of the steerable stylet wire of FIG. 1.

FIGS. 2 and 3 illustrate details of the distal segment 24. The distal segment 24 preferably comprises an elongated coil 30 comprising space-wound coil turns wound about a longitudinal coil axis 40 in a coil length extending between a proximal coil end at junction 26 to a distal coil end at distal stylet wire end 28.

The coil 30 is preferably fabricated of wire or slotted tubing that is rectangular in cross-section and wound into a flat-wound coil such that the width of the wire is greater than the thickness of the wire measured radially. A coil spacing SP separates the space-wound coil turns apart. The coil 30 is preferably formed of a wrought stainless steel, more preferably a precipitation hardened stainless steel such as PH15-7 Mo or 17-7PH or similar alloys, such as Mp35N, which, in their annealed condition are readily weldable and which may be shaped by precision stamping and coiling. The coil 30 is preferably confined with a thin-walled polyimide sheath 32.

The coil proximal end is mounted to the tubular member distal end to support the coil 30 in axial alignment with the elongated tubular member of the proximal segment 22, whereby a stylet wire lumen 29 is defined extending between the stylet wire proximal end within handle 12 and stylet wire distal end 28 by the axial alignment of the tube lumen and the coil lumen.

An elongated pull (or push-pull) movable wire 34 (shown in FIGS. 2 and 3) extends from movable wire proximal end affixed to a tensioning mechanism within handle 12 through the stylet wire lumen 29 to a movable wire distal end that is affixed to the coil distal end at the stylet wire distal end 28. The handle knob 16 is manipulated to apply tension to the movable wire 34. In accordance with the present invention, the rotation or distal advancement of spinner or knob 16 relative to the handle portion 14 causes deflection of two or more distal portions of distal segment 24 to a compound curve configuration as illustrated in FIGS. 1 and 4.

In FIG. 1, a first longitudinal portion 36 and a second longitudinal portion 38 of distal segment 24 are caused to bend in opposite directions with respect to axis 40 to induce a compound curvature in the distal segment 24 as shown in broken lines when the movable wire is retracted or pulled proximally through the stylet wire lumen. The first and second longitudinal portions 36 and 38 can have any desired length and are displaced apart longitudinally along the distal segment by any desired spacing, which can include some overlapping of the first and second longitudinal portions 36 and 38. The bending of the first and second longitudinal portions 36 and 38 is effected by interposing spacers between the adjacent coil turns of a plurality of coil turns in first and second lines that are substantially parallel with the axis 40 and one another. When the movable wire 34 is pushed, the tension tends to expand or widen the spacing SP except where the spacing SP is maintained by the spacers. Similarly, when movable wire 34 is pulled, the tension tends to compress or eliminate the spacing SP except where the spacing SP is maintained by the spacers.

For example, a first line 42 of spacers $44_1$–$44_m$ shown in FIG. 2 is formed that maintains the coil spacing SP between a first plurality "m" of coil turns extending in the first longitudinal portion 36 of the coil 30 and distal segment 24. The spacing SP is maintained when the longitudinally extending movable wire 34 is pulled proximally through the coil lumen, whereby a first curve is induced in the coil turns of the first longitudinal portion 36 in a first radial direction $R_1$ away from the coil axis 40.

Similarly, a second line 46 of spacers $48_1$–$48_n$ shown in FIG. 3 is formed that maintains the coil spacing SP between a second plurality "n" of coil turns extending in the first longitudinal portion 38 of the coil 30 and distal segment 24. The spacing SP is maintained when the longitudinally extending movable wire 34 is pulled proximally through the coil lumen, whereby a second curve is induced in the coil turns of the second longitudinal portion 38 in a second radial direction $R_2$ away from the coil axis 40.

The spacers $44_1$–$44_m$ of first line 42 are illustrated as being located between each adjacent coil turn of FIG. 2, but it will be understood that spacers $44_1$–$44_m$ can be distributed in patterns leaving it possible to expand or compress the spacing SP between certain coil turns. Such an alternative pattern is illustrated by line 46 of spacers $48_1$–$48_n$ of FIG. 3, where n=10, in this illustration.

The first line 42 of spacers extends along a side of the coil 30 that is displaced from the axis 40 in a line displacement radius $r_1$ that is diametrically opposite to the radial direction of the curve $R_1$. The second line 42 of spacers extends along a side of the coil 30 that is displaced from the axis 40 in a line displacement radius $r_1$ that is diametrically opposite to the radial direction of the curve $R_1$. In other words, the first and second spacer lines 42 and 44 are circumferentially displaced from one another around the coil 30 by 180° as shown in FIGS. 4 and 5, and the radial directions $R_1$ and $R_2$ are also circumferentially displaced from one another around the coil 30 by 180°.

Thus, in the embodiment of FIGS. 1–3, a compound, S-shape, curve of the distal segment 24 is effected by inducing the first and second curves in first and second portions 36 and 38 by pulling or pushing movable wire 34 from handle 12. The first curve is induced in the radial direction $R_1$ from the coil axis 40, and the second curve is induced in the second radial direction $R_2$ from the coil axis 40 that is diametrically opposite to the radial direction $R_1$. Therefore, the compound, S-shape, curve of the distal segment 24 is in two directions in substantially a single plane.

FIGS. 6–9 illustrate the distal segment 24' of a further deflectable stylet 10' according to the present invention which is formed as described above with respect to FIGS. 1–3. However, first, second and third lines 50, 52 and 54 of spacers 56, 58 and 60 are provided that are circumferentially displaced from one another around the circumference of the coil 30 and distal segment 24 by 120° as shown in FIGS. 7, 8 and 9, respectively. The first, second and third lines 50, 52 and 54 of spacers 56, 58 and 60 are distributed in first, second and third portions 62, 64 and 66 of the distal segment 24' that are substantially longitudinally displaced from one another along the length of distal segment 24'. When the pull wire 34 is retracted, orthogonal bends are formed in the distal segment 24' in the first, second and third portions 62, 64 and 66 of the distal segment 24' to bend distal segment 24' in three substantially orthogonal X, Y, and Z directions.

From the above, it may be appreciated that any number of lines of spacers between coil turns can be formed extending lengthwise in discrete portions of the distal segment and radially displaced from one another around the circumference of the distal segment.

Figure 6:
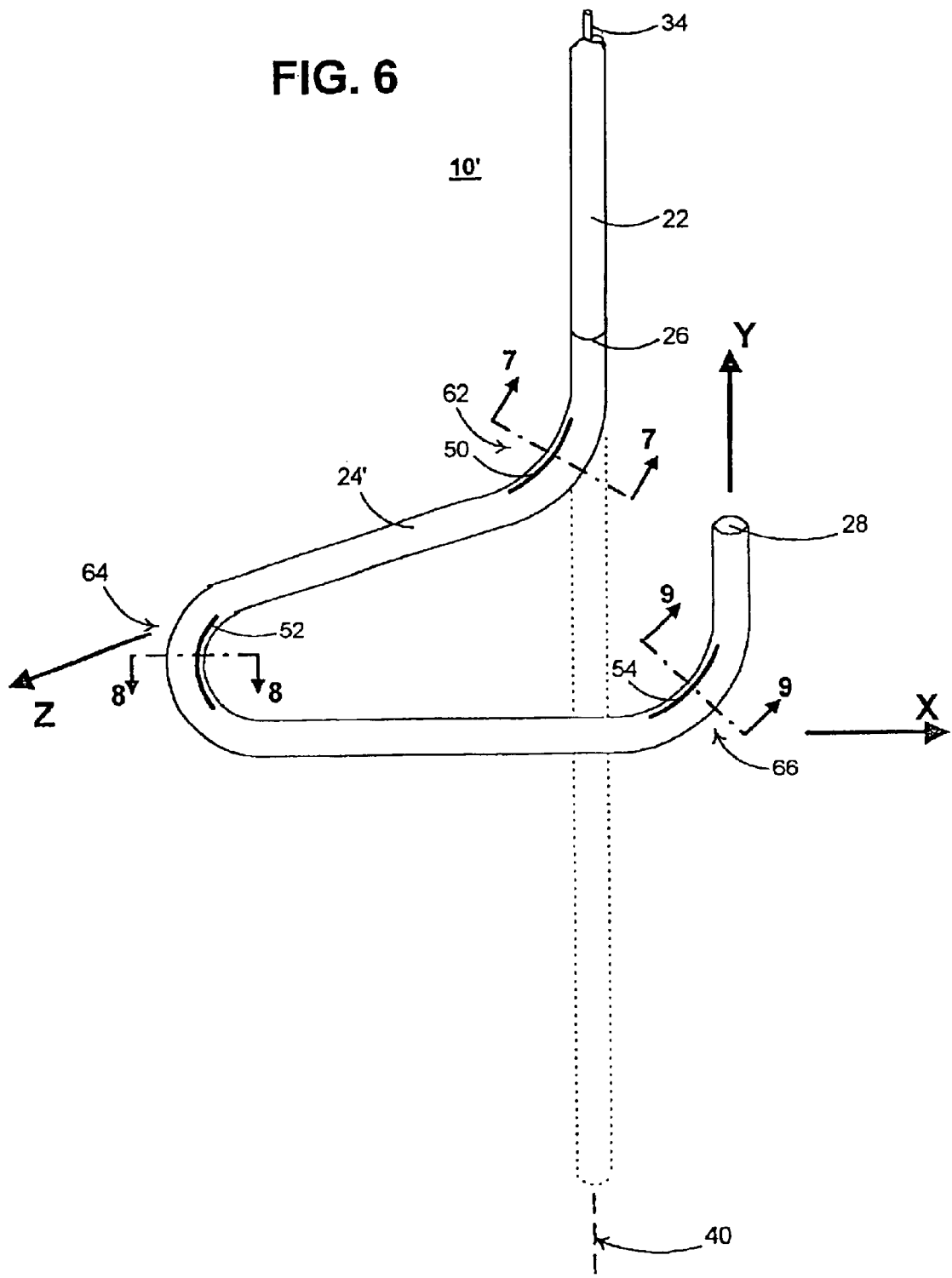
FIG. 6 is a plan view of the distal segment of a steerable stylet wire in accordance with a second embodiment of the present invention capable of forming a compound, substantially three-dimensional, curve in three longitudinally spaced portions of the distal segment of the stylet wire.

A single movable wire 34 extending through the lumen 29 from the handle 12 to the stylet wire distal end 28 is depicted in FIGS. 1 and 6 to induce the above-described curves. However, it will be understood that separate elongated pull (or push-pull) movable wires can extend through lumen 29 to selectively induce curves in the portions 36 and 38 of the stylet wire 20 and portions 62, 64 and 66 of the stylet wire 20' of FIG. 6. FIGS. 10 and 11 depict the distal segment 24 of a steerable stylet wire 20 of stylet 10" in accordance with a variation of the embodiments of the present invention employing separate movable wires 34 and 34' for each portion 36 and 38 of the distal segment 24. The distal ends of the movable wires 34 and 34' are attached to the coil 30 distally to portions 36 and 38, respectively. The movable wires 34 and 34' are both pushed distally away from the handle 12 to induce a deflection of the distal tip 28 and curves in portions 36 and 38 as shown in FIG. 10. The movable wires 34 and 34' are both pulled proximally toward the handle 12 to induce a deflection of the distal tip 28 and curves in portions 36 and 38 as shown in FIG. 11.

Figure 12:
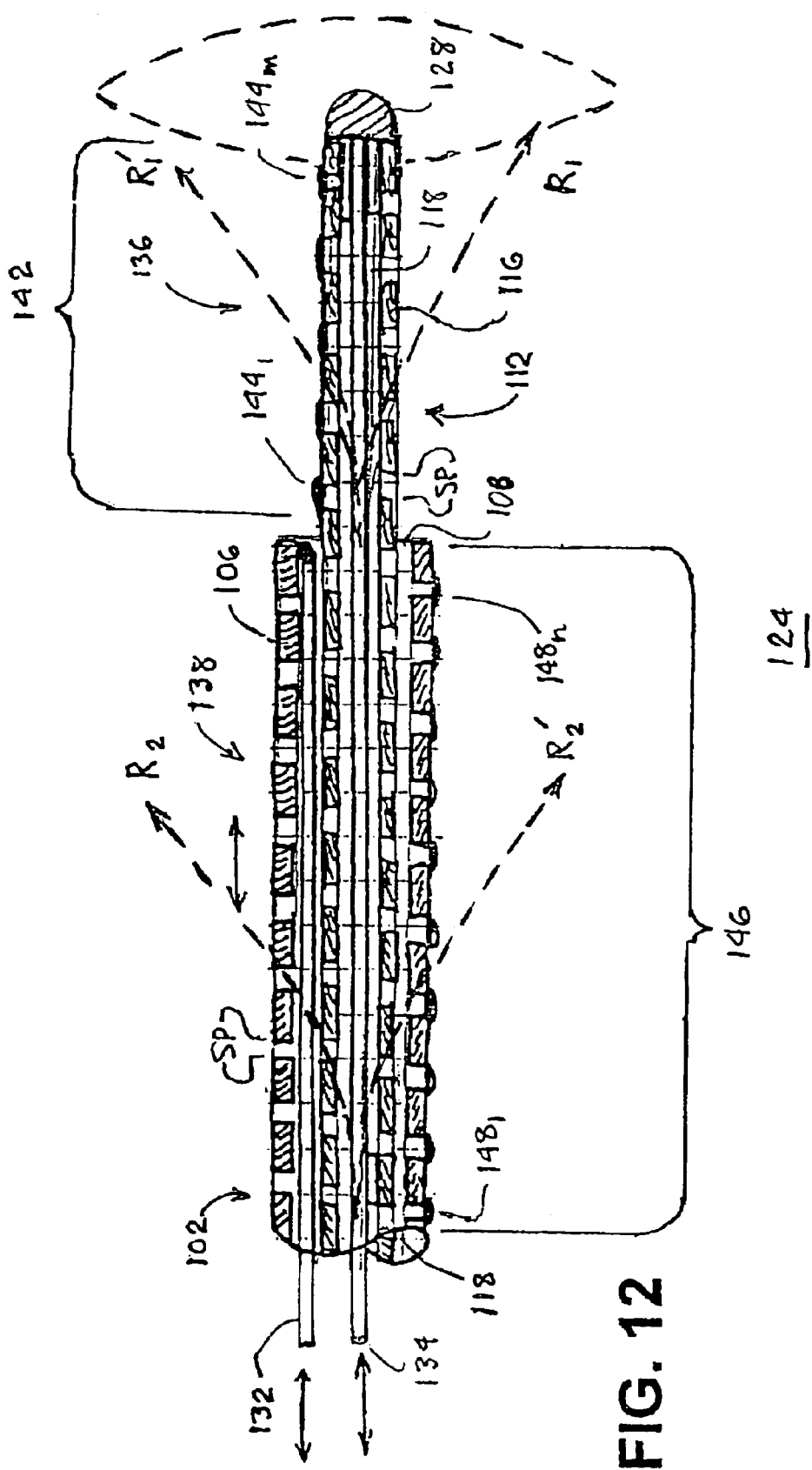
FIG. 12 is a plan view in partial cross-section depicting the distal segment of a steerable stylet wire in accordance with a further variation of the embodiments of the present invention employing inner and outer co-axially nested deflectable wires each deflectable through movable wires.

In a further variation depicted in FIG. 12, the longitudinally displaced curves are formed in respective distal portions of a stylet wire 120 of a stylet wire distal segment 124 that is formed of outer and inner deflectable wires 102 and 112, respectively. The distal segment of outer deflectable wire 102 is formed of a spirally wound flat wire 106 forming an outer lumen 104 and having an open distal end 108. The distal segment of inner deflectable wire 112 is also formed of a spirally wound flat wire 116 forming an inner lumen 118 and having a closed distal end 128. The proximal portions of inner and outer deflectable wires 112 and 102 can be formed as described elsewhere herein.

The inner deflectable wire 112 is extended through the outer lumen 104 so that the inner and outer deflectable wires 102 and 112 can be moved axially relative to one another, and the inner deflectable wire 112 can be rotated within the outer lumen 104.

An inner movable wire 134 extends through the inner lumen 118 and is attached to the closed distal end 128 of the inner deflectable wire 112. Similarly, an outer movable wire 132 extends through the outer lumen 118 alongside the inner deflectable wire 112 and is attached to the open distal end 108 of the outer deflectable wire 102.

A first line 142 of spacers $144_1$–$144_m$ extending in the first longitudinal distal portion 136 of the inner deflectable wire 112 maintains the coil spacing SP between a first plurality "m" of coil turns of the inner deflectable wire coil 116. The spacing SP is maintained when the longitudinally extending inner movable wire 134 is pulled proximally through the inner coil lumen 118, whereby a bend is induced in the coil turns of the longitudinal portion 136 in a radial direction $R_1$ away from the stylet wire axis. Similarly, the spacing SP is maintained when the longitudinally extending inner movable wire 134 is pushed distally through the inner coil lumen 118, whereby a bend is induced in the coil turns of the longitudinal portion 136 in a radial direction $R_1'$ away from the stylet wire axis.

A second line 146 of spacers 148$_1$–148$_n$ extending in the second longitudinal distal portion 138 of the outer deflectable wire 102 maintains the coil spacing SP between a second plurality "n" of coil turns of the outer deflectable wire coil 106. The spacing SP is maintained when the longitudinally extending outer movable wire 132 is pulled proximally through the inner coil lumen 118, whereby a bend is induced in the coil turns of the longitudinal portion 138 in a radial direction $R_2$ away from the stylet wire axis. Similarly, the spacing SP is maintained when the longitudinally extending outer movable wire 132 is pushed distally through the outer coil lumen 104, whereby a bend is induced in the coil turns of the longitudinal portion 138 in a radial direction $R_2'$ away from the stylet wire axis.

The outer and inner deflectable wires 102 and 112 can be rotated with respect to one another so that the first and second lines 142 and 146 of spacers 144$_1$–144$_m$ and 148$_1$–148$_n$ can be displaced at any radial angle with respect to one another. For example, the inner deflectable wire 112 can be rotated within the outer lumen 104 so that the distal tip 128 can aimed in any chosen radial direction when deflected to the angles $R_1$ or $R_1'$. The spacers are depicted schematically in the figures and can be formed in a variety of ways. Although the lines 42, 46, 50, 52, 54 of spacers are depicted as parallel to one another and axis 40, it will be understood that the lines 42, 46, 50, 52, 54 can extend spirally in a predetermined arc around the circumference of the wire coils. Such a spiral line can cause the portion of the distal segment to assume a spiral or helical shapes when the movable wire is pulled.

The spacers can be discrete components or can be coupled together in the manner of a backbone as described in the above-referenced commonly assigned '338 patent. In a first alternative embodiment, the spacers can be formed by welding adjacent coil turns-together in each line 42, 46, 50, 52, 54, 142, 146. In this embodiment, the wire coil or coils are formed of a material such as the PH15-7 Mo or 17-7PH stainless steels, or MP35N, in a ductile (annealed) condition. Such stainless steels are compressible, and portions of the coil turns along a side of the coil can be compressed in a line 42, 46, 50, 52, 54, 142, 146. The compressed coil turns each form axial projections that bridge the spacing SP and contact or engage one another. The adjacent projections so formed may simply bridge the space between the coil turns through length of the line, whereby the spacing SP is maintained in the line when the movable wire 34, 124, 134 is pulled and retracted. The adjoining tabs or projections so formed may alternatively be welded together so that spreading of the spacing SP is inhibited if the movable wire 34, 124, 134 is pushed and operates as a push-pull wire. In this embodiment, it is preferable that the tabs or projections are formed such that their base width is greater than the arc height of the section of the coil across which the tabs extend, in order to provide increased resistance to out of plane twisting of the coil during longitudinal movement of the internal movable wire 34, 124, 134. Alternatively, the spacers can be formed simply by filling the space SP with solder or by welding the coil sides together in a line at each location where fixation is desired.

In further embodiments, a the coil wire turns can be welded to a linear attachment mechanism, e.g., one or more a short weld supply wire extending along the line internally within the coil lumen of the type disclosed in the above-referenced '620 patent, or a shaped backbone member or backbone of the types disclosed in the above-referenced, commonly assigned '338 patent. The short wire or backbone can be flattened and welded in a line to the interior or the exterior of the coil turns of the coil. The short wires welded inside the coil lumen are preferably circular in cross-section or flattened in cross-section to conform to the inside coil curvature to minimize obstruction of the lumen and maximize weld contact with the coil turns.

Or the short wires can be shaped to be rectangular or arcuate as shown by short wires 49 and 51 of FIGS. 14 and 15 to present a flat or arcuate side toward the lumen. The movable wire 34, 124, 134 can be flattened on a side facing the flattened side of the short wires 49 and 51 to maximize the space between the movable wire 34, 124, 134 and the short wires 49, 51 as also shown in FIGS. 14 and 15.

The width of the weld of the short weld supply wire to the coiled wire turns along the line 42, 46, 50, 52, 54, 142, 146 is preferably controlled to provide adequate torque strength so that the distal segment can be twisted through rotation of the stiffer proximal segment from the handle or proximal portion without causing the distal segment to kink. Thus, the weld width can be in the range subtending a 60° to 90° arc, for example. Welding a pair of small diameter weld supply wires 45, 47 side-by-side to the coil turns in a line as depicted in FIG. 13, can attain such a weld width.

The short wires can also be formed as a backbone of the type disclosed in the above-referenced '338 patent that are provided with laterally extending projections which are sized to fit between adjacent turns of the coil in a line allowing compression or expansion of the coil only along the opposite side of the coil in response to longitudinal movement of the internal push/pull wire. The projections of the backbone also prevent relative longitudinal movement of individual turns of the coil along the side of the coil engaging the backbone, providing a smooth, continuous bend. The backbone preferably has a generally arcuate configuration in cross section, and has a width substantially greater than its arc height in order to provide a preferred bending axis and prevent out of plane twisting of the deflectable portion of the stylet or guidewire during longitudinal movement of the internal push/pull wire.

In a further embodiment of the '338 patent, the backbone takes the form of a tube having external threads formed thereon which correspond to the spaces between the turns of the coil. In this embodiment, the tube is provided with a longitudinal slot or recess such that over a portion of the length of the tube, the tube engages the coil only along one side thereof, allowing compression or expansion of the coil only along the opposite side of the coil in response to longitudinal movement of the internal wire. In this embodiment, the backbone also has a generally arcuate configuration in cross section along the length of the slot, and along this length also has a width substantially greater than its arc height in order to provide a preferred bending axis and prevent out of plane twisting of the deflectable portion of the stylet or guidewire during longitudinal movement of the internal wire. The backbone is preferably coupled to the coil at its tip and may optionally be welded to the coil along its length, at the points at which the projections of the backbone contact individual turns of the coil.

The welding of the coil turns together while maintaining the spacing SP can also be effected employing wire feed welding equipment that applies a weld supply wire 55 to the exterior of the wire coil and applies welding energy as shown in FIG. 16, the applied force and energy causes the weld supply wire 55 to melt and flow into the space SP between coil wire turns as depicted in FIG. 17. The technique of FIGS. 16 and 17 can be employed alone or in conjunction with the use of any of the above-described internally disposed backbones or short wires.

In all embodiments in which wrought stainless steels as discussed above or similar materials are employed for the coil and backbone, the coil and backbone are preferably fabricated from the metal in its annealed, relatively softer ductile condition, allowing winding of the coil without substantial spring-back and facilitating any required stamping or forming operations performed on the coil or backbone. The coil and backbone are then preferably welded to one another. Following assembly of the coil and backbone assembly and any welding of the components to one another, the assembly is preferably heat treated and stress relieved to temper the assembly and produce a desired final set of mechanical embodiments, properties (hardness, spring constant, tensile strength, etc.). In some cases, the tubing making up the majority of the stylet body may also be formed of such alloys and welded to the coil and core, preferably prior to heat treatment.

In all of the above-described embodiments, the proximal segment 22 can be formed in a number of ways other than from a solid tube. The proximal segment 22 and the distal segment 24, 24', 24" and each distal segment of outer and inner deflectable wires 102 and 112 can be formed of a continuous coiled wire, preferably a coiled flat wire. The turns of the proximal segment can be tightly wound or attached together at selected circumferentially displaced adjacent turns in any of the manners disclosed in the above-referenced '830 patent to make the proximal segment 22 torqueable while retaining flexibility. The spaced coil windings can be welded together in three parallel lines each offset at 120 degrees, for example, to create torque control while maintaining flexibility.

It will also be understood that the present invention can be implemented in a guidewire wherein the handle 12 is eliminated and the movable wire 34 or wires 124, 134 extends out of the lumen opening at the stylet wire proximal end. The exposed section of the movable wires 34, 124, 134 can be manually grasped while holding the exposed section of the proximal segment to exert tension in the distal segment to form the curves described above to facilitate advancement of the stylet wire distal end 28 through tortuous pathways.

CONCLUSION

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments. It will also be understood that there may be other structures, functions and operations ancillary to the typical operation of elongated medical instruments that are not disclosed and are not necessary to the practice of the present invention.

In addition, it will be understood that specifically described structures, functions and operations set forth in the above-referenced patents can be practiced in conjunction with the present invention, but they are not essential to its practice.

It is therefore to be understood, that within the scope of the appended claims, the invention may be practiced otherwise than as specifically described without actually departing from the spirit and scope of the present invention.

What is claimed is:

1. A deflectable elongated medical instrument, comprising:
    an elongated tubular member having proximal and distal tubular member ends;
    a wire coil comprising coil turns wound about a longitudinal coil axis in a coil length extending between proximal and distal coil ends, the coil turns separated apart by a coil spacing, the coil proximal end joined to the tubular member distal end to support the coil in axial alignment with the elongated tubular member;
    a longitudinally extending movable wire mounted within the coil and tubular member, the movable wire mechanically coupled at or near the distal end of the wire coil and extending proximally through the coil and tubular member to the tubular member proximal end;
    first means for maintaining the coil spacing between a first plurality of coil turns extending in a first line in a first longitudinal portion of the coil when the movable wire is pulled proximally through the coil whereby a first curve is induced in the coils of the first longitudinal portion in a first radial direction from the coil axis; and
    second means for maintaining the coil spacing between a second plurality of coil turns extending in a second line in a second longitudinal portion of the coil when the movable wire is pulled proximally through the coil, the second longitudinal portion longitudinally displaced at least in part from the first longitudinal portion along the coil length, the second longitudinal portion displaced circumferentially from the first longitudinal portion, whereby a second curve is induced in the coils of the second longitudinal portion in a second radial direction from the coil axis differing from the first radial direction.

2. The deflectable elongated medical instrument of claim 1, wherein the first and second radial directions are substantially diametrically opposed.

3. The deflectable elongated medical instrument of claim 2, wherein:
    the first means couples the coil turns together in the first line in the first longitudinal portion of the coil to inhibit separation of the coupled coil turns when the movable wire is pushed distally through the coil; and
    the second means couples the coil turns together in the second line in the second longitudinal portion of the coil to inhibit separation of the coupled coil turns when the movable wire is pushed distally through the coil.

4. The deflectable elongated medical instrument of claim 1, wherein;
    the first means couples the coil turns together in the first line in the first longitudinal portion of the coil to inhibit separation of the coupled coil turns when the movable wire is pushed distally through the coil; and
    the second means couples the coil turns together in the second line in the second longitudinal portion of the coil to inhibit separation of the coupled coil turns when the movable wire is pushed distally through the coil.

5. The deflectable elongated medical instrument of claim 1, further comprising:
    third means for maintaining the coil spacing between a third plurality of coil turns extending in a third line in a third longitudinal portion of the coil when the movable wire is pulled proximally through the coil, the third longitudinal portion longitudinally displaced at least in part from the first and second longitudinal portions along the coil length, the third longitudinal portion displaced circumferentlally from the first and second longitudinal portions, whereby a third curve is induced in the coils of the third longitudinal pardon in a third radial direction from the coil axis differing from the first and second radial directions.

6. The deflectable elongated medical instrument of claim 5, wherein the first, second, and third radial directions are substantially equally separated radially apart along the circumference of the coil.

7. The deflectable elongated medical instrument of claim 6, wherein:
the first means couples the coil turns together in the first line in the first longitudinal portion of the coil to inhibit separation of the coupled coil turns when the movable wire is pushed distally through the coil;
the second means couples the coil turns together in the second line in the second longitudinal portion of the coil to inhibit separation of the coupled coil turns when the movable wire is pushed distally through the coil; and
the third means couples the coil turns together in the third line in the third longitudinal portion of the coil to inhibit separation of the coupled coil turns when the movable wire is pushed distally through the coil.

8. The deflectable elongated medical instrument of claim 1, wherein the elongated tubular member and the wire coil are formed of a single elongated wire coil having proximal and distal segments, and the wire coil turns in the proximal segment are tightly wound and/or welded together at discrete spaced apart longitudinally and radially oriented locations.

9. A deflectable elongated medical instrument, comprising:
an elongated tubular member having proximal and distal ends and a member lumen;
a wire coil having proximal and distal coil ends and a coil lumen, the coil proximal end joined to the distal end of the tubular member;
a longitudinally movable wire mounted within the aligned member and coil lumens and mechanically coupled at or near the distal end of the coil, the movable wire having a flattened surface; and
a backbone located within a portion of the coil lumen, extending along one side of the coil and mechanically coupled to the a plurality of turns of the wire coil to maintain the spacing between coil turns and induce a bend in the portion of the coil when the movable wire is pulled or pushed, the backbone having a width greater than its are height and presenting a flattened or arcuate surface facing the flattened surface of the movable wire extending alongside the backbone.

10. A elongated medical instrument of claim 9, wherein the backbone is mechanically coupled to individual turns of the coil intermediate the proximal and distal ends of the coil.

11. The deflectable elongated medical instrument of claim 9, wherein the elongated tubular member and wire coil are formed of: a resin-based material and a metallic material, repectively, and the wire coil turns in a proximal segment are tightly wound to create torque control while maintaining flexibility.

12. The deflectable elongated medical instrument of claim 9, wherein the elongated tubular member and wire coil are formed of: a polyimide material and a stainless steel material, respectively, and the wire coil turns in a proximal segment are tightly wound and/or welded together at discrete spaced apart longitudinal and radial locations.

13. The deflectable elongated medical instrument of claim 9, wherein the proximal elongated tubular members and the wire coils of the inner and outer deflectable wires are each formed of a single elongated wire coil having proximal and distal segments, and the wire coil turns in the proximal segment are tightly wound and/or welded together at spaced apart longitudinal and radial locations to create torque control while maintaining flexibility.

14. A deflectable elongated medical instrument, comprising;
an elongated tubular member having proximal and distal tubular member ends;
a wire coil comprising coil turns wound about a longitudinal coil axis in a coil length extending between proximal and distal coil ends, the coil turns separated apart by a coil spacing, the coil proximal end joined to the tubular member distal end to support the coil in axial alignment with the elongated tubular member;
first means for maintaining the coil spacing between a first plurality of coil turns extending in a first line in a first longitudinal portion of the coil;
a first longitudinally extending movable wire mounted within the coil and tubular member, the first movable wire mechanically coupled at or near the distal end of the first longitudinal portion of the wire coil and extending proximally through the coil and tubular member to the tubular member proximal end to induce a first curve in the first longitudinal portion in a first radial direction from the coil axis when the movable wire is pulled proximally through the coil;
second means for maintaining the coil spacing between a second plurality of coil turns extending in a second line in a second longitudinal portion of the coil; and
a second longitudinally extending movable wire mounted within the coil and tubular member, the second movable wire mechanically coupled at or near the distal end of the second longitudinal portion of the wire coil and extending proximally through the coil and tubular member to the tubular member proximal end to induce a second curve in the second longitudinal portion in a second radial direction from the coil axis when the movable wire is pulled proximally through the coil.

15. The deflectable elongated medical instrument of claim 14, wherein the first and second radial directions are substantially diametrically opposed.

16. The deflectable elongated medical instrument of claim 15, wherein:
the first means couples the coil turns together in the first line in the first longitudinal portion of the coil to inhibit separation of the coupled coil turns when the first movable wire is pushed distally through the coil; and
the second means couples the coil turns together in the second line in the second longitudinal portion of the coil to inhibit separation of the coupled coil turns when the second movable wire is pushed distally through the coil.

17. The deflectable elongated medical instrument of claim 14, wherein:
the first means couples the coil turns together in the first line in the first longitudinal portion of the coil to inhibit separation of the coupled coil turns when the first movable wire is pushed distally through the coil; and the second means couples the coil turns together in the second line in the second longitudinal portion of the coil to inhibit separation of the coupled coil turns when the second movable wire is pushed distally through the coil.

18. The deflectable elongated medical instrument of claim 14, wherein the elongated tubular member and the wire coil are formed of:
a resin-based material and a stainless steel material, respectively, and a plurality of the wire coil turns welded together at discrete spaced apart longitudinal and radial locations.

19. A deflectable elongated medical instrument comprising:
an outer deflectable wire comprising:
a proximal elongated tubular member having proximal and distal ends and a tubular member lumen;
a distal wire coil having proximal and distal coil ends and a coil lumen, the coil proximal end joined to the distal end of the tubular member and the aligned tubular member and coil lumens forming an outer deflectable wire lumen;
a backbone extending along one side of the wire coil and mechanically coupled to a plurality of turns of the wire coil to maintain the spacing between coil turns; and
a longitudinally inner movable wire mounted within the outer deflectable wire lumen and mechanically coupled to the distal wire coil substantially distal to the backbone to induce a bend in the portion of the distal wire coil when the inner movable wire is pulled or pushed;

an inner deflectable wire comprising:
a proximal elongated tubular member having proximal and distal ends and a tubular member lumen;
a distal wire coil having proximal and distal coil ends and a coil lumen, the coil proximal end joined to the distal end of the tubular member and the aligned tubular member and coil lumens forming an outer deflectable wire lumen;
a backbone extending along one side of the wire coil and mechanically coupled to a plurality of turns of the wire coil to maintain the spacing between coil turns; and
a longitudinally inner movable wire mounted within the outer deflectable wire lumen and mechanically coupled to the distal wire coil substantially distal to the backbone to induce a bend in the portion of the distal wire coil when the inner movable wire is pulled or pushed; and wherein:
the inner deflectable wire is extendable through the outer deflectable wire lumen enabling the independent formation of bends in the portions of the distal wire coils of the inner and outer deflectable wires upon pulling or pushing of the inner and outer movable wires.

20. The deflectable elongated medical instrument of claim 19, wherein the inner deflectable wire is rotatable within the outer deflectable wire lumen enabling the independent formation of bends that are radially displaced form one another in the portions of the distal wire coils of the inner and outer deflectable wires upon pulling or pushing of the inner and outer movable wires.

* * * * *